(12) United States Patent
Zatirukha

(10) Patent No.: US 12,708,372 B2
(45) Date of Patent: Aug. 18, 2026

(54) STYPTIC HARNESS TOURNIQUET

(71) Applicant: Volodymyr Zatirukha, Dnipro (UA)

(72) Inventor: Volodymyr Zatirukha, Dnipro (UA)

( * ) Notice: Subject to any disclaimer, the term of this patent is extended or adjusted under 35 U.S.C. 154(b) by 0 days.

(21) Appl. No.: 19/117,416

(22) PCT Filed: Nov. 4, 2022

(86) PCT No.: PCT/UA2022/000064
§ 371 (c)(1),
(2) Date: Apr. 1, 2025

(87) PCT Pub. No.: WO2024/085850
PCT Pub. Date: Apr. 25, 2024

(65) Prior Publication Data

US 2026/0007414 A1 Jan. 8, 2026

(30) Foreign Application Priority Data

Oct. 21, 2022 (UA) .............................. u 2022 03935

(51) Int. Cl.
*A61B 17/132* (2006.01)

(52) U.S. Cl.
CPC .................................. *A61B 17/132* (2013.01)

(58) Field of Classification Search
CPC .............. A61B 17/132; A61B 17/1322; A61B 17/1327
See application file for complete search history.

(56) References Cited

U.S. PATENT DOCUMENTS

2012/0071917 A1* 3/2012 McDonald .............. G01L 5/102 116/212
2021/0153873 A1* 5/2021 Peterson ............ A61B 17/1322

FOREIGN PATENT DOCUMENTS

RU 205951 U1 8/2021
UA 151561 U 8/2022

* cited by examiner

*Primary Examiner* — Darwin P Erezo
*Assistant Examiner* — Raihan R Khandker

(57) ABSTRACT

A styptic harness tourniquet includes a casing with Velcro fastener. The casing contains a sling with windlass rod, and a buckle and a base on which a fixator and a strap are located. The buckle contains at least two holes, and the base contains at least six holes. The strap contains at least one hole. At least one hole of the buckle and at least two holes of the base contain teeth. At least one fixator of the buckle is located on the casing. At least two limiters are located on the fixator of the windlass rod. The holes in the buckle are arranged in at least two rows. At least one strengthening element is connected to the sling for at least one sixth of its length, and at least two protectors are located in the casing on both sides of the base.

10 Claims, 4 Drawing Sheets

STYPTIC HARNESS TOURNIQUET

RELATED APPLICATIONS

This application is a National Phase of PCT Patent Application No. PCT/UA2022/000064 having International filing date of 4 Nov. 2022, which claims the benefit of priority Ukrainina patent application number u202203935 filed on Oct. 21, 2022.

TECHNICAL FIELD

The invention belongs to the field of medicine, primarily to medical equipment, as a styptic harness tourniquet that is applied with one or two hands, and can be used in first aid to stop external arterial bleeding from injured limbs.

BACKGROUND ART

Esmarch's rubber hemostatic tourniquets are known. The disadvantage of such tourniquets is the inability of controlling compression, as a result of which pain occurs when tightening it. In addition, such tourniquets do not allow you to put them on with one hand and need to be loosened and tightened again.

A known hemostatic tourniquet, that contains an elastic band with a fringe effect on one side, a device for forming a loop with the fringe inward and a device for fixing the applied tourniquet, and the device for forming a loop is made in the form of a buckle-frame of a rectangular shape, and a device for fixing the applied tourniquet is located on the free end of the band and consists of at least 2.5 turns (RF Patent No. 76791, i. cl. A6ˆ17/12, publ. 10 Oct. 2008).

The disadvantage of the known hemostatic tourniquet is the high probability of excessive compression of the injured limb and pinching of the skin of the injured limb. In addition, the disadvantage of the known tourniquet is the insufficient reliability and duration of fixation of the free end of the belt strap after applying the tourniquet.

A known hemostatic tourniquet containing a non-extensible tape, an extensible tape in the form of a rubber element connected to two steel rectangular rings on two sides, with rectangles and the inscriptions "Thigh", "Shoulder" applied to it, and a windlass rod, at the same time non-extensible the ribbon forms a double loop when the tourniquet is applied, and the windlass rod is made with a notch in the middle and cone-arrow shaped ends (RF Patent No. 76791, i. cl. A6ˆ17/12, publ. 10 Oct. 2008).

The disadvantage of the known hemostatic tourniquet is the high probability of excessive compression of the injured limb and pinching of the skin of the injured limb. In addition, the disadvantage of the known tourniquet is the lack of reliability of fixing the windlass rod after applying the harness with the possibility of injury to the limb when the tape is punctured by the windlass rod.

A known hemostatic tourniquet, which contains a belt strap, at one end of which a buckle is fixed, and at the other end a tip is made, slings located in the inner cavity of the belt strap and have fixed ends, and a node for tightening and fixing the applied tourniquet, the node for tightening and fixing of the applied tourniquet is installed in the center of the belt strap and contains a base on which an indicator of the time of application of the tourniquet and a coil with the possibility of rotation are located, in the central hole of which a lever is located, on the side surface of the coil on both sides of the lever, radial axes with central slotted notches are made and disk-shaped sided guides, in addition, on both edges of the base in front of the coil and behind it, radially oriented notches are made, while the slings of the belt strap are successively stretched through the slit in front of the coil, the slit in the radial axis of the coil and the slit in the back of the coil (RF Patent No. 2531449, i. cl. A61B17/12, publ. 20 Oct. 2014).

The disadvantage of the known hemostatic tourniquet is the difficulty of performing the tightening and fixing of the tourniquet, which complicates the process of applying and tightening the tourniquet, resulting in the possibility of excessive compression of the injured limb and pinching of the skin of the injured limb. In addition, the disadvantage of the known tourniquet is the insufficient reliability and duration of fixation of the free end of the belt strap after applying the tourniquet.

A known hemostatic tourniquet, which contains a belt strap, on one end of which a buckle is fixed, and on the other end a tip is made, a sling, which is located in the inner cavity of the belt strap and has fixed ends, and a knot for tightening and fixing the applied tourniquet; the belt strap is formed by the initial part, inside which two inserts are fixed overlapping with the possibility of moving one along the other, and the long part, on which a textile Velcro® fastener is additionally fixed on the front side, made in the form of a tape, on which loop and hook sections are diagonally located alternately, or in the form of a tape, where the loops and hooks are mixed, and the node for tightening and fixing the tourniquet clamp consists of a windlass rod with a notch and a fixator of the windlass rod, which are fixed on the front side of the initial part of the belt strap, while on the front side of the initial part of the strap the tape has two notches with a frame of the fixator of the windlass rod located above them, which connects the adjacent ends of the sections formed by the notches of the initial part of the belt strap, the windlass rod is placed above the frame of the fixator of the windlass rod, and through the specified two notches through the frame of the fixator of the windlass rod the sling is brought out and brought through the notch in windlass rod turning stick with the possibility of twisting it to tighten the belt strap, followed by fixing one of the ends of the windlass rod in the fixator of the windlass rod; the fixator of the windlass rod has a triangular shape and contains two protrusions to limit the movement of the windlass rod; the fixator of the windlass rod is fixed on the surface of the initial part of the belt strap with the help of a short tape; the frame of the fixator of the windlass rod has a rectangular shape; inserts in the initial part of the belt strap have a rectangular shape and are made of plastic; on one of the ends of the belt strap, a tape is additionally fixed, made with the possibility of applying an inscription with sharp objects; additionally contains a textile fastener, made in the form of Velcro® with the possibility of fixation the windlass rod and the free end of the belt strap after applying the tourniquet; Velcro® is made with the possibility of writing with sharp objects or a marker; the tip of the belt strap is additionally equipped with a plastic insert; the buckle is made in the form of a metal double rectangular frame with a jumper, which has teeth for fixing the tourniquet; the belt strap is made with a width of 4 cm and a length of 93 cm; the sling is made with a width of 2 to 2.5 cm; the sling is made of textile fabrics; textile fastener and belt strap are made of textile or polyamide fabrics; the windlass rod and the fixator of the windlass rod are made of duralumin or steel (UA Patent No. 103336, i. cl. A61B 17/12, publ. 10 Dec. 2015, Bull. No. 23).

The disadvantages of the known hemostatic tourniquet are low reliability and efficiency of operation.

A known military harness tourniquet, which contains a casing with a Velcro® fastener, in which an inner band with a plastic windlass rod is located; at the end of the casing is a plastic one-hole unidirectional buckle and a four-hole stabilization plate with a windlass clip and a windlass strap (Access Mode: http://www.combattourniquet.com/).

The disadvantages of the well-known harness tourniquet for military purposes are the low reliability of the design and the low efficiency of its operation due to the too thin and soft casing and when used (twisting the windlass rod) causes pain when applying, the lower tape of the casing is located on the surface of the base, which in some cases can lead to winding under the windlass rod together with the sling of the lower tape of the casing and self-blocking, which leads to incomplete coverage of the blood flow, the casing with Velcro® is too soft, which does not give a stable loop when applying and can interfere with self-medication.

The closest Prior art to the claimed styptic harness tourniquet is a styptic harness tourniquet containing a cover with a Velcro® fastener, in which a tape is located; at one end of the casing there is a buckle and a base on which the fixator (hereinafter the fixator of the windlass rod) and the strap of the fixator (hereinafter the strap of fixator of the windlass rod) are located; the windlass rod is attached to the tape; the casing has at least two layers, the buckle contains at least one hole, the base contains at least six holes, the strap of the fixator contains at least one hole; the holes of the buckle and the base contain teeth on at least one side; the material of the base and the fixator can be plastic, plastic or others; the material of the turning stick and buckle can be aluminum, aluminum alloys, plastic, etc.; the teeth of the holes can have a rectangular, rounded, trapezoidal, square shape; the windlass rod has at least 1 cm of smooth surface and at least 1.5 cm of ribbed surface at the edges (UA Patent No. 151561, i. cl. A61B 17/12, publ. Aug. 10, 2022, Bull. No. 32).

The disadvantages of this styptic harness tourniquet are the low reliability of the design and the low efficiency of its operation due to the thin and soft tape, which, in the event of incorrect application of the hemostatic tourniquet with an incomplete first round during the twisting of the tourniquet, in some cases can lead to unreliable fixation, which leads to an incomplete overlap of blood flow, the part of the casing between the buckle and the base is too soft, when applying and twisting the stick-turner in the plane between the base and the buckle, the skin may be pinched, which may lead to additional injury.

RU 205 951 U1 discloses a tourniquet having a casing, a buckle, a base, and a windlass rod. US 2021/153873 A1 discloses a further tourniquet.

THE INVENTION

The object of the invention is to create such styptic harness tourniquet, in which, due to structural changes, it is possible to increase the reliability of the structure, increase the efficiency of its operation, reduce pain during application, and reduce the risks of additional injury to soft tissues and vascular and nervous system. pinch.

The object is achieved by the fact that styptic harness tourniquet, that consists of a casing with a Velcro® fastener, in which a sling is located; at one end of the casing there is a buckle and a base on which the fixator and the strap of the fixator are located; a windlass rod is attached to the sling; the casing has at least two layers, the buckle contains at least two holes, the base contains at least six holes, the strap of the fixator contains at least one hole; at least one hole of the buckle and at least two holes of the base on at least one side contain teeth, at least one strengthening element is added and connected to the sling for at least one sixth of its length, at least two protectors are located in the casing on both sides of the base; at least one fixator of the buckle located on the casing, at least two limiters are located on the fixator of windlass rod, holes in the buckle are arranged in at least two rows:

- the strengthening element can be a tape, braid or other.
- the material of the base and the fixator of the windlass rod can be plastic or other.
- the material of the windlass rod can be aluminum, aluminum alloys, duralumin, plastic, or other.
- the material of the buckle can be metal or plastic.
- the material of the protectors can be ethylene vinyl acetate (EVA), tape, fabric, or other.
- the teeth of the holes can have a rectangular, rounded, trapezoidal, square shape.
- the windlass rod contains at least 1 cm of smooth surface and at least 1.5 cm of ribbed surface at the edges.
- the material of the fixator of the buckle can be plastic, synthetic paper or other.
- there are limiters for installing the hard part of the Velcro® fastener on the fixator of the windlass rod, which are higher than the base of the fixator by at least 0.5 mm.

Figure 1:
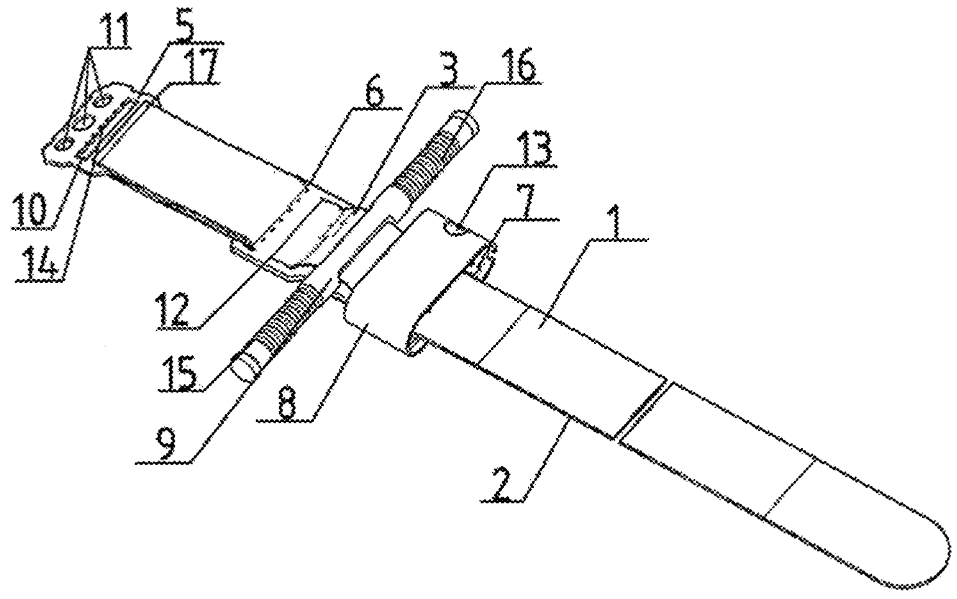
FIG. 1 depicts the general view of the styptic harness tourniquet.
Figure 2:
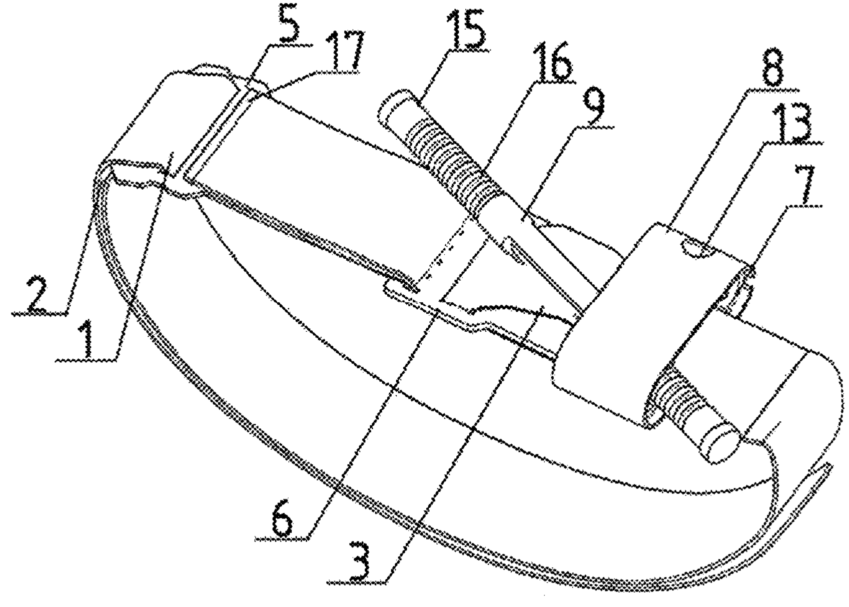
FIG. 2 depicts the styptic harness tourniquet ready for use.
Figure 3:
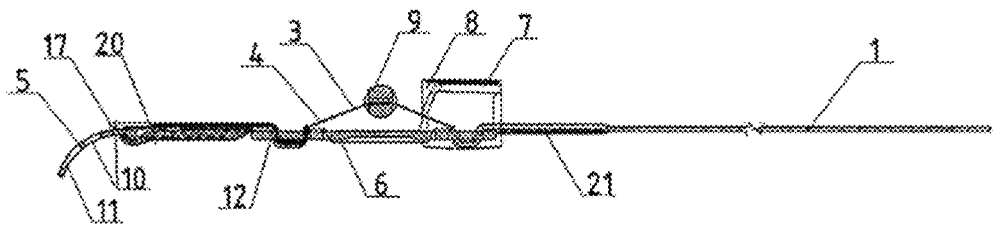
FIG. 3 depicts a cross sectional view of the casing with protectors and fixator of the buckel.
Figure 4:
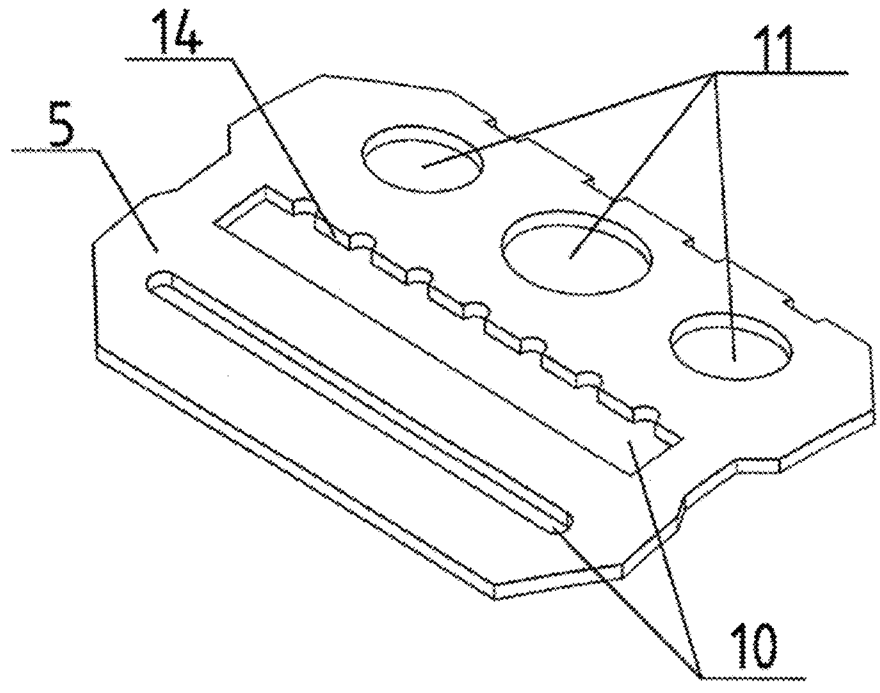
FIG. 4 depicts the general view of the buckle.
Figure 5:
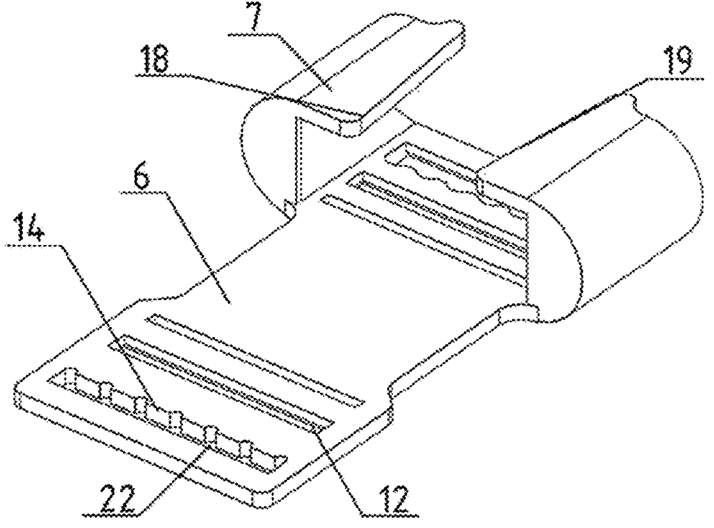
FIG. 5 depicts the general view of the base.
Figure 6:
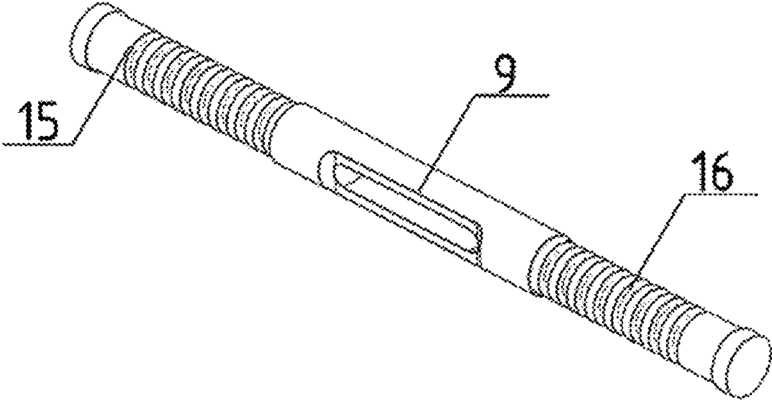
FIG. 6 depicts the general view of the windlass rod.
Figure 7:
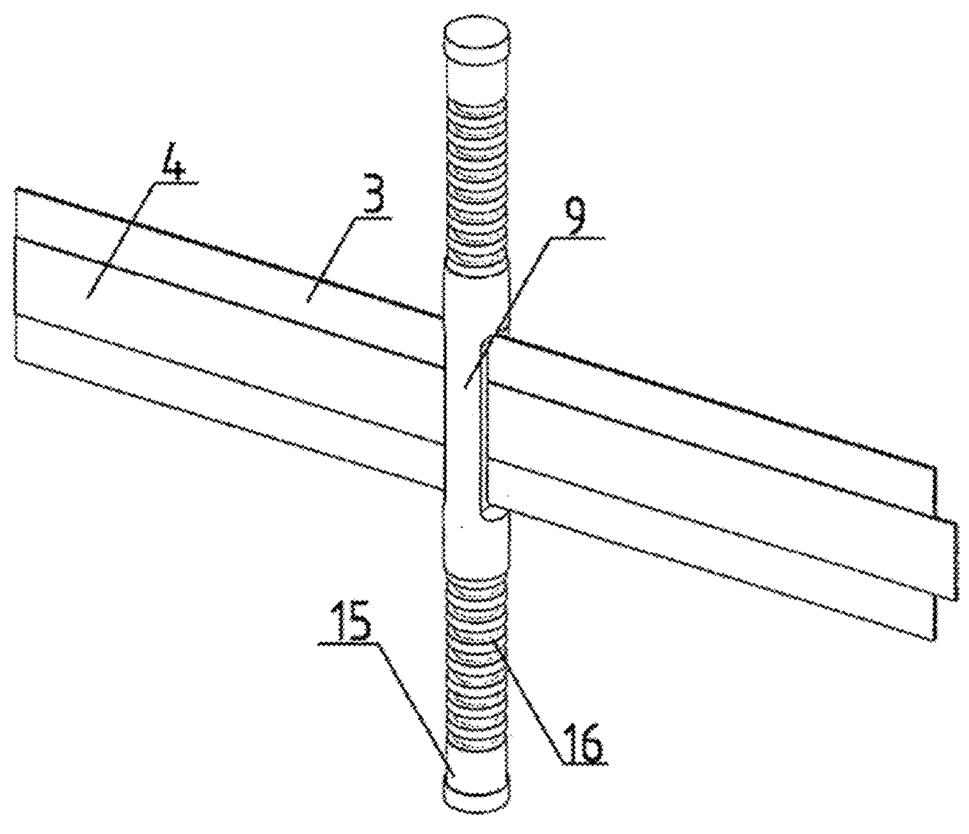
FIG. 7 depicts the general vies og the sling with a strenthening elewmnt.

FIG. 1 shows the general view of the styptic harness tourniquet, FIG. 2 shows a styptic harness tourniquet in a ready-to-use form, FIG. 3 shows a cross-section of the casing with protectors and a fixator of the buckle, FIG. 4 shows the general view of the buckle, FIG. 5 shows the general view of the base, FIG. 6 shows the general view of the windlass rod, FIG. 7 shows the general view of a sling with a strengthening element.

A styptic harness tourniquet (example) consists of a casing 1 with a Velcro® fastener (2), in which a sling (3) is located with a strengthening element (4) located on one sixth of its length. At the end of the casing (1) there is a buckle (5) with a fixator (17) of the buckle and a base (6) on which the fixator (7) with limiters (18) (19) and the strap (8) of the fixator are located. Protectors (20, 21) are located in the casing on both sides of the base. The windlass rod (9) is fixed on the sling (3) with a strengthening element (4). The buckle contains three rows of two holes (10) and three holes (11) (example). The base contains four holes (12) and two holes (22). The strap (8) of the fixator (7) contains at least one hole (13). The hole (10) of the buckle and the holes (22) of the base on at least one side contain teeth (14) that have a rectangular shape (example). The windlass rod (9) has 1 cm of smooth surface (15) and 2 cm of ribbed surface (16) at the edges.

A styptic harness tourniquet is used as follows. On the injured limb (not shown in the drawing), a casing 1 with a Velcro® fastener 2 is placed perpendicular to the limb, the end of which is threaded through one hole 10 (example) of the buckle 5 with the fixator 17 of the buckle 5 and tightened strongly. After that, with the help of the windlass rod 9, by rotating it, tighten the sling 3 with the strengthening element 4, which is located in the casing 1. After tightening the sling 3 in order to squeeze the arteries and stop the bleeding, the windlass rod 9 is placed in the fixator 7 with limiters 18, 19, which is located on the base 6. After placing the windlass rod 9 in the fixator 7, it is covered with the remaining end of the casing 1 and fixed with a strap 8 of the fixator 7 with a hole 13, which is provided by 1 cm of a smooth surface 15 and 2 cm of ribbed surface 16. The base 6 contains four holes 12 and two holes 22 through which the cover 1 passes with a hook-and-loop fastener 2 (hybrid or preceding loop/hook) in such a way as to allow it to pass under the base 6 without contact the base 6 with the human body (not shown in the drawing) and the sling 3 that remains on the surface of the base 6. The holes 10 of the buckle 5 and the holes 22 of the base 6 at least on one side contain teeth 14 that have a rectangular in the form (example), which provide tighter and more reliable fixation of the casing 1 with a Velcro® fastener 2. The protectors 20, 21 are located in the casing 1 on both sides of the base 6, allow reducing pain and provides more comfortable operating conditions, as they reduce the pressure from the casing 1 and make it impossible to pinch soft tissues between the buckle 5 and the base 6. The holes 11 of the buckle 5 reduce the weight of the buckle 5 and make it possible to lighten the weight of the product as a whole. The fixator 17 of the buckle 517 allows you to fix the buckle 5 when the casing 1 is pulled through it, which allows you to do it quickly and conveniently, preventing the buckle from lifting up.

Modern hemostatic tourniquets are widely used in the medical field. Therefore, their development and improvement is an urgent task.

Existing structural solutions of hemostatic tourniquets have a number of disadvantages, the main ones of which are low reliability and low efficiency of operation. So, for example, the CAT hemostatic tourniquet (Access mode: http://www.combattourniquet.com/) has low reliability and operational efficiency due to a too thin and soft casing and when used (twisting the windlass rod) causes pain at application, the lower band of the casing is located on the surface of the base, which in some cases can lead to winding under the windlass rod together with the sling of the lower band of the casing and self-blocking, which leads to incomplete overlap of the blood flow, the casing with Velcro® is too soft, which does not provide a stable loops and can interfere with self-help. The buckle, the windlass rod and the base are made of plastic, which has low operational qualities. The buckle and base have a small number of holes. The lower belt of the casing is located on top of the base, which does not allow them to avoid contact with the human body. When applying and twisting the windlass rod in the plane between the base and the buckle, the skin can be pinched; this can lead to additional injury. In addition, the buckle holes and base do not provide a tight fit on the limb, thus not providing reliable hemostasis.

The well-known styptic harness tourniquet (prototype, UA Patent No. 151561, i. cl. A61B 17/12, publ. 10 Aug. 2022, Bull. No. 32) has a number of disadvantages, since the sling that passes through the casing has insufficient strength and when improper application of a styptic harness tourniquet with an incomplete first round when twisting the tourniquet windlass rod in some cases lead to unreliable fixation. The base and casing create additional pressure during operation on the injured human limb.

The developed styptic harness tourniquet allows you to eliminate shortcomings and significantly increase the reliability and efficiency of operation thanks to the introduced structural elements and connections. By introducing at least one reinforcement element connected to the sling, a buckle retainer and at least two protectors located on either side of the base. The strengthening element connected to the sling significantly improves its strength during operation. Protectors made of ethylene vinyl acetate (EVA, example), located in the casing on both sides of the base, make it possible to reduce additional injuries to soft tissues and vascular-nerve bundles of a person and create more comfortable conditions for operation. The holes on the buckle are located in at least two rows, which allows you to significantly reduce its weight and ensure greater reliability and convenience during operation, and the fixator prevents it from bending upwards when inserting the casing relative to the tape into the buckle, which allows you to quickly insert the tourniquet casing into the buckle hole even in uncomfortable conditions.

The styptic harness tourniquet has experimental samples that have been tested by volunteers and received favorable review.

What I claimed is:

1. A styptic harness tourniquet that consists of a casing (1) with a hook-and-loop fastener (2), in which a sling (3) is located; wherein at one end of the casing (1) there is a buckle (5) and a base (6) on which a fixator (7) and a strap (8) of the fixator (7) are located; wherein a windlass rod (9) is attached to the sling (3); wherein the casing (1) has at least two layers, the buckle (5) contains at least two holes (10), and the base (6) contains at least six holes (12, 22), wherein the strap (8) of the fixator (7) contains at least one hole (13); wherein at least one hole (10) of the buckle (5) and at least two holes (22) of the base (6) on at least one side contain teeth (14), wherein at least one fixator (17) of the buckle (5) is located on the casing (1), wherein at least two limiters (18, 19) are located on the fixator (7) of the windlass rod (9), wherein the holes (10) in the buckle (5) are arranged in at least two rows, wherein at least one strengthening element (4) is added and connected to the sling (3) for at least one sixth of its length, and at least two protectors (20, 21) are located in the casing (1) on both sides of the base (6).

2. The styptic harness tourniquet according to claim 1, wherein the strengthening element (4) is a tape or braid.

3. The styptic harness tourniquet according to claim 1, wherein the material of the base (6) and the fixator (7) of the windlass rod (9) is plastic.

4. The styptic harness tourniquet according to claim 1, wherein the material of the windlass rod (9) is aluminum, aluminum alloys, duralumin, or plastic.

5. The styptic harness tourniquet according to claim 1, wherein the material of the buckle (5) is metal or plastic.

6. The styptic harness tourniquet according to claim 1, wherein the material of the protectors (20, 21) is ethylene vinyl acetate (EVA), tape, or fabric.

7. The styptic harness tourniquet according to claim 1, wherein the teeth (14) of the holes (22) can have a rectangular, rounded, trapezoidal, or square shape.

8. The styptic harness tourniquet according to claim 1, wherein the windlass rod (9) contains at least 1 cm of smooth surface (15) and at least 1.5 cm of ribbed surface (16) at the-edges of the windlass rod (9).

9. The styptic harness tourniquet according to claim 1, wherein the material of the fixator (17) of the buckle (5) is plastic or synthetic paper.

10. The styptic harness tourniquet according to claim 1, wherein the at least two limiters (18, 19) for installing a hard part of the hook-and-loop fastener (2) on the fixator (7) of the windlass rod (9), which are higher than the base (6) of the fixator (7) by at least 0.5 mm.

* * * * *